US00PP31272P2

(12) United States Plant Patent
Hansen

(10) Patent No.: US PP31,272 P2
(45) Date of Patent: Dec. 24, 2019

(54) ***PHLOX* PLANT NAMED 'PURPLE SPRITE'**

(50) Latin Name: ***Phlox* hybrid**
Varietal Denomination: Purple Sprite

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/350,524

(22) Filed: Nov. 28, 2018

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./320
See application file for complete search history.

*Primary Examiner* — Susan McCormick Ewoldt

(57) ABSTRACT

A new and unique cultivar of hybrid creeping phlox named *Phlox* 'Purple Sprite' multi-stemmed, short, upright, slowly-spreading habit with clean, green, glossy, lanceolate to linear leaves with exceptional powdery mildew resistance. Flowers are bright purple with small near-white eye and dark purple markings nearly covering the top of the plant in peak flowering season about one week later than typical *Phlox subulata*. 'Purple Sprite' is especially useful as a containerized plant and for the flower garden.

1 Drawing Sheet

Botanical classification: *Phlox* hybrid.
Variety denomination: 'Purple Sprite'.

STATEMENT REGARDING PRIOR DISCLOSURES UNDER 37 CFR 1.77(b)(6)

The first public disclosure of the claimed plant, in the form of a sale, was made by Walters Gardens, Inc. on Jul. 9, 2018. Prior to that, on Nov. 28, 2017 the claimed plant was displayed as a photograph without description in a calendar of Walters Gardens, Inc., who obtained the plant and all information relating thereto, from the inventor. No plants of *Phlox* 'Purple Sprite' have been sold, in this country or anywhere in the world, nor has any disclosuie of the new plant been made, more than one year prior the filing date of this application, and such sale or disclosure within one year was either derived directly or indirectly from the inventor.

BACKGROUND OF THE INVENTION

The present invention relates to a new and distinct cultivar of *Phlox* plant, known as *Phlox* 'Purple Sprite' and will be referred to hereafter by its cultivar name or the "new plant". The new plant was the result of a cross made by the inventor between *Phlox subulata* 'North Hills' (not patented) as the female or seed parent and *Phlox stolonifera* 'Sherwood Purple' as the male or pollen parent at a wholesale perennial nursery in Zeeland, Mich. on Mar. 6, 2014. The new plant was given the breeder code 14-270-1 prior to naming and throughout subsequent evaluations at the same nursery. 'Purple Sprite' has been asexually propagated by stem cuttings in the greenhouses at the same nursery in Zeeland, Mich. since 2016. The unique characteristics of the new plant have been found to be reproducible and stable in successive generations of asexually propagated plants and the resultant plants have been found to be identical to the original selection.

BRIEF SUMMARY OF THE PLANT

*Phlox* 'Purple Sprite' is unique from its parents and all other creeping *Phlox* or other *Phlox* known to the inventor.

The new plant differs from the female parent, 'North Hills', in that the female parent has near-white colored flowers with dark violet eye zone beginning about one week earlier, the plants are shorter, the foliage is more linear and the growth rate faster and less manageable in the landscape. The male parent, 'Sherwood Purple', has light lavender-purple flowers with less mound coverage, the foliage is more ovate, and the habit is taller and more open. The closest comparison cultivars known to the inventor are 'PHL090201' U.S. Plant Pat. No. 26,854 ('Jagger'), 'PPPHL07301' U.S. Plant Pat. No. 23,702 ('Angelina'), 'PPPH07201' U.S. Plant Pat. No. 23,705 ('Paris') and PHL090401' U.S. Plant Pat. No. 26,852 ('Levine'). 'PHL090201' has a dark purple flower with narrower petals that do not overlap. 'PPPHL07301' has lighter lavender flowers and is slightly taller. 'PPPH07201' has a lighter pinkish lavender flower with petals that do not overlap and the habit is taller. 'PHL090401' has a medium lavender flower with narrower petals that do not overlap. 'Purple Sprite' differs from all other *phlox* known to the inventor in the following repeatedly observed traits in combination:

1. Plants of short mounded habit, slowly spreading by short rhizomes, producing clean, glossy, clean green, lanceolate to linear leaves;
2. Showing exceptional powdery mildew resistance;
3. Multiple branched, stems produce rounded mounds of flowers starting in mid-spring;
4. Faintly-sweet fragrant flowers on mounded stems of about 15.0 cm tall;
5. Flowers are bright purple flower faces with small near-white eye zones and markings;
6. Flowers cover nearly the entire top of the plant;
7. Flowering about one week after typical *Phlox subulata* cultivars.

BRIEF DESCRIPTION OF THE DRAWINGS

The photographs of the new plant demonstrate the unique traits of 'Purple Sprite' and the overall appearance of the plant at two-years-old grown in a full-sun trial garden in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
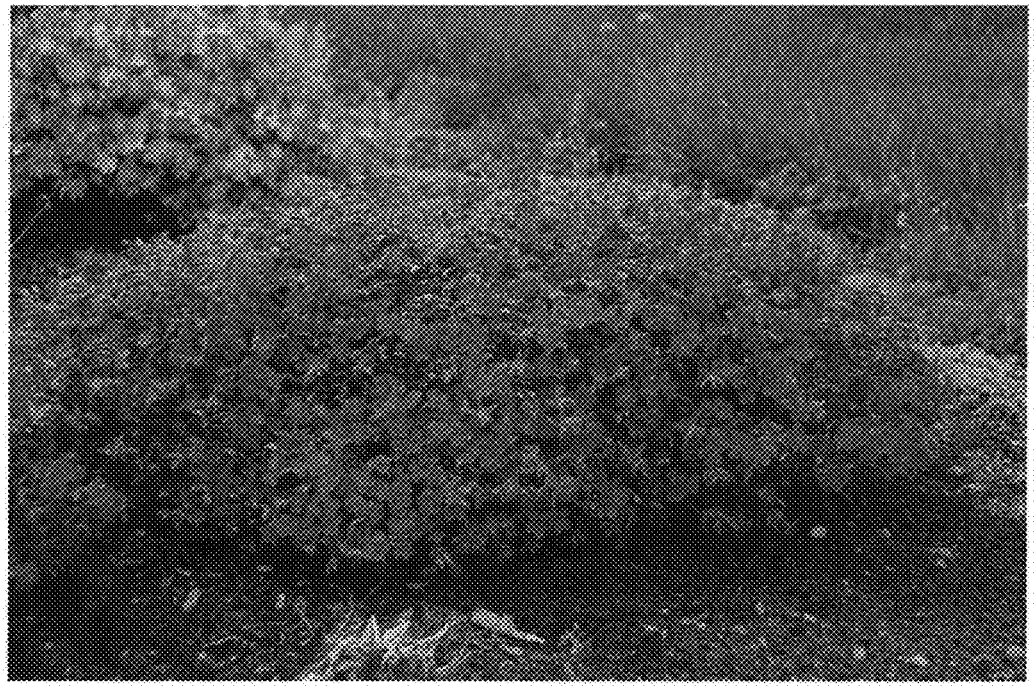
FIG. 1 shows the habit of the new plant in peak flower.
Figure 2:
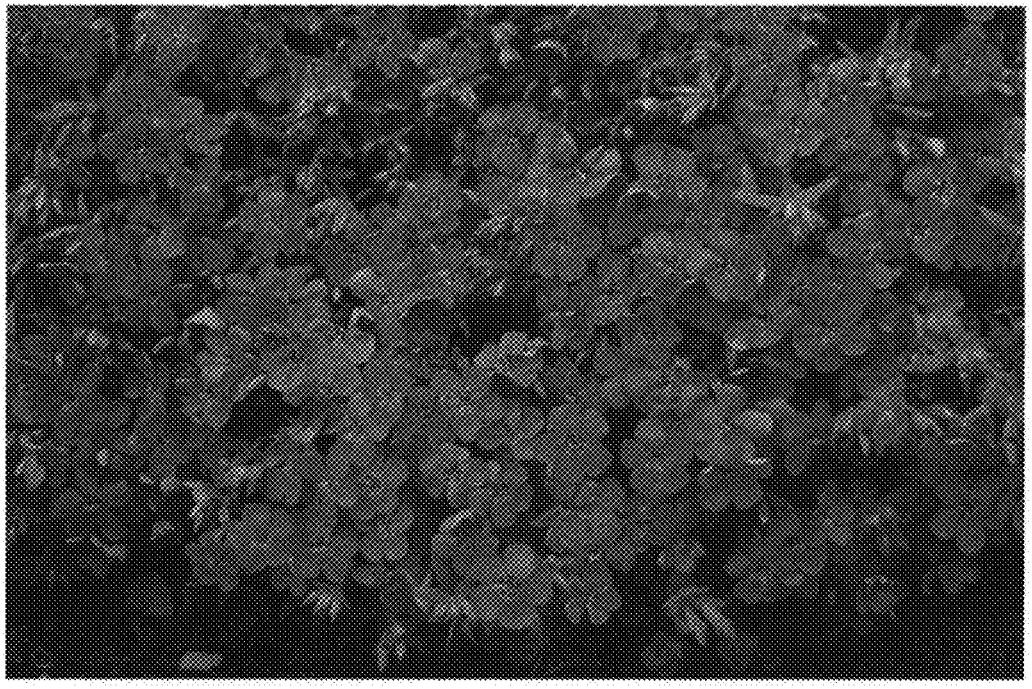
FIG. 2 shows a close-up of the flowers and buds.

The following descriptions and color references are based on The 2015 edition of The Royal Horticultural Society Colour Chart except where common dictionary terms are used. *Phlox* 'Purple Sprite' has not been observed under all possible environments. The phenotype may vary slightly with different growing environments such as temperature, light, fertility, soil pH, moisture and maturity levels, but without any change in the genotype. The following observations and size descriptions are based on two-year-old plants in the full-sun trial garden of a wholesale perennial nursery in Zeeland, Mich. with supplemental fertilizer and water as needed.

Botanical classification: *Phlox* hybrid;

Parentage: Female or seed parent *Phlox subulata* 'North Hills' and the male or pollen parent *Phlox stolonifera* 'Sherwood Purple';

Plant habit: Densely-mounded, winter-hardy, herbaceous perennial, producing branched stems and early spring flowering; about 15.0 cm tall and about 20.0 cm wide; flowering about one week after typical *Phlox subulata* cultivars and continuing for about 4 weeks;

Propagation: Stem cuttings; rooting in about 14 days;

Time to produce finished crop in 3.8 liter pots: About 12 to 14 weeks; moderate rate of growth;

Root: Primary roots to about 1.0 mm thick; secondary fibrous and freely branching; color creamy white to tan depending on soil type and root stage of development;

Leaves: Simple; opposite; lanceolate to linear; entire margin; narrowly acute apex; attenuate base; sessile;

Leaf size: To about 22.5 mm long by about 6.5 mm wide, average about 16.0 mm long by about 5.0 mm wide;

Leaf surfaces: Glabrous and slightly lustrous abaxial and adaxial;

Leaf color expanding: Adaxial and abaxial between RHS N144A and RHS 145A;

Leaf color at flowering: Adaxial between RHS 146B and RHS 146A, abaxial nearest RHS 146D;

Foliage fragrance: None detected;

Veins: Pinnate; glabrous adaxial and abaxial; midrib about 0.5 mm wide at base, slightly sunken adaxial and raised abaxial; color same as surrounding leaf tissue;

Petiole: Leaves sessile;

Stems: Cylindrical; flexible; strong; pubescent; average about 12.0 cm long and 2.5 mm diameter at base;

Stem color: Young stems nearest RHS 138B with blush of nearest RHS 183D; becoming nearest RHS N186C;

Nodes: About nine per stem below terminal flowers; average internode length about 1.3 cm;

Node color: Nearest RHS N186C;

Inflorescence: A loosely-branched compound corymb of about 20 flowers; about 8.0 cm long and 6.0 cm across;

Flowers: Perfect; salverform with flat face and long fused corolla tube; actinomophic; typically with five petals; about 14.0 mm long total with tube about 12.5 mm long; face about 13.0 mm across; attitude upright to outwardly;

Flower longevity: About 5 days; self-cleaning;

Flower fragrance: Faintly sweet;

Buds one to two days prior to opening: Narrowly oblanceolate, to nearly clavate; acute apex with convolute petals; base fused; about 12.5 mm long and 2.5 mm diameter in tube and swollen to 5.0 mm diameter toward apex of convolute petals;

Bud color: Exposed petals nearest RHS N82D and RHS 86D;

Petals: Five; limb obtuse, apex rounded and emarginate; base fused into tube; margin entire; abaxial limb and tube glabrous, adaxial limb glabrous, adaxial tube glabrous except pubescent in region about 3.0 mm to 7.0 mm from base;

Petal size: Basal 12.5 mm fused into corolla tube, to a diameter of about 3.0 mm; limb face about 6.0 mm across, and face about 6.0 mm long; imbricate toward center;

Petal color: Adaxial face nearest RHS N82B developing small light center halo lighter than RHS 85D, and two dark purple marks of nearest RHS 79B toward center; abaxial limb nearest RHS N82D; adaxial tube nearest RHS 145C toward base with pubescence nearest RHS NN155D and distally nearest RHS 76C, abaxial tube basal 3.0 mm nearest RHS 145C distally nearest RHS 86D;

Androecium:

*Filaments.*—Typically five; adnate to adaxial petals except free in terminal 1.0 mm; varying lengths between 3.0 mm and 7.0 mm, less than 0.5 mm in diameter; white, nearest RHS NN155D.

*Anther.*—Five; oblong elliptic; basifixed; longitudinal; about 1.2 mm long by 0.7 mm wide; color nearest RHS 23B.

*Pollen.*—Abundant; color nearest RHS 17A.

Gynoecium: One pistil per flower; to about 12.0 mm long;

*Style.*—Cylindrical; about 8.0 mm long and less than 0.5 mm diameter; color base nearest RHS 145D, distal section nearest RHS 76B.

*Stigma.*—Trifurcate in the distal 1.0 mm, less than 0.25 mm in diameter; persistent after flower abscission; color nearest RHS 150D.

*Ovary.*—Superior; globose; about 2.0 mm long and 2.0 mm diameter; color blend between RHS 144A and RHS N144A.

Calyx: Tubular; adpressed to corolla tube proximally and slightly reflexed distally; to about 5.0 mm long and 4.5 mm wide at apex;

Sepals: Five; linear; narrowly acute apex, margin entire; basal 3.0 mm fused; surface matte and glabrous abaxial, lustrous and glabrous adaxial; individually about 5.0 mm long and 1.0 mm wide;

Sepal color: Abaxial center nearest RHS NN137C with light blushing nearest RHS N186C and margins in fused region and distally nearest RHS 196D; adaxial nearest RHS 146D distally and 145B proximally;

Peduncle: Pubescent; flexible, strong, mostly upright; cylindrical; flowering portion about 6.0 cm long and 2.5 mm diameter at base of flower branches; branches to about 5.0 cm long and 2.0 mm diameter at base; typically five flowers per branch;

Peduncle color: Nearest blend between of RHS 183A and RHS N186C;

Pedicel: Terete; glabrous; to about 6.0 mm long and 1.0 mm diameter;

Pedicel color: Nearest blend between of RHS 178D and RHS 183D;

Fruit and seeds have not yet been observed;

Hardiness and culture: The new plant grows best with plenty of moisture and adequate drainage; prefers full sun but tolerates light shade; is hardy to at least from USDA zone 3 through 8.

Disease and pest resistance: *Phlox* 'Purple Sprite' demonstrated the excellent resistance to powdery mildew caused by *Erysiphe cichoracearum* under conditions of intense pressure that would normally show symptoms.

I claim:

1. A new and distinct cultivar of hybrid *phlox* plant named *Phlox* 'Purple Sprite', as herein described and illustrated.

* * * * *